United States Patent [19]
Mazzoni et al.

[11] Patent Number: 5,847,163
[45] Date of Patent: Dec. 8, 1998

[54] PROCESS FOR THE TRANSFORMATION OF A VANADIUM/PHOSPHORUS MIXED OXIDE CATALYST PRECURSOR INTO THE ACTIVE CATALYST FOR THE PRODUCTION OF MALEIC ANHYDRIDE

[75] Inventors: Gianluca Mazzoni, Torre Boldone; Fabrizio Cavani, Modena; Giancarlo Stefani, Gorle/Bergamo, all of Italy

[73] Assignee: Lonza SPA, Milan, Italy

[21] Appl. No.: 841,761

[22] Filed: Apr. 28, 1997

[30] Foreign Application Priority Data

Apr. 29, 1996 [IT] Italy ................................. MI96A0836

[51] Int. Cl.[6] .......................... C07D 307/60; B01J 27/18
[52] U.S. Cl. ............................................ 549/233; 502/209
[58] Field of Search .............................. 549/233; 502/209

[56] References Cited

U.S. PATENT DOCUMENTS

| | | | |
|---|---|---|---|
| 3,915,892 | 10/1975 | Harrison | 252/435 |
| 3,985,775 | 10/1976 | Harrison | 252/435 |
| 4,511,670 | 4/1985 | Suciu et al. | 502/209 |
| 4,594,433 | 6/1986 | Suciu et al. | 549/256 |
| 4,654,425 | 3/1987 | Suciu et al. | 549/259 |
| 4,668,652 | 5/1987 | Fumagalli et al. | 502/209 |
| 5,137,860 | 8/1992 | Ebner et al. | 502/209 |

OTHER PUBLICATIONS

*Rompp Chemie Lexikon*, 9th Edition, Georg Thieme Verlag, Stuttgart, vol. 4, p. 3285.

*Primary Examiner*—Amelia Owens
*Attorney, Agent, or Firm*—Fisher, Christen & Sabol

[57] ABSTRACT

A vanadium/phosphorus mixed oxide catalyst precursor is transformed into the active catalyst for the production of maleic anhydride. The activation takes place in a fluidized bed and includes the steps of (a) initially heating the precursor; (b) further heating under superatmospheric pressure; (c) isothermal stage at superatmospheric pressure; and, finally, (d) cooling the activated catalyst obtained. Catalysts activated according to this procedure show high performance in the conversion of non-aromatic hydrocarbons to maleic anhydride.

24 Claims, No Drawings

PROCESS FOR THE TRANSFORMATION OF A VANADIUM/PHOSPHORUS MIXED OXIDE CATALYST PRECURSOR INTO THE ACTIVE CATALYST FOR THE PRODUCTION OF MALEIC ANHYDRIDE

BACKGROUND OF THE INVENTION

1. Field Of The Invention

The invention relates to a process for the transformation of a vanadium/phosphorus mixed oxide catalyst precursor into the active catalyst for the production of maleic anhydride and to a process for the production of maleic anhydride applying such activated catalyst. Maleic anhydride is a very important intermediate for manufacturing unsaturated polyester resins or a versatile intermediate for producing pharmaceuticals and agrochemicals.

2. Background Art

Numerous catalysts based on a vanadium/phosphorus mixed oxide substantially in the form of vanadyl pyrophosphate are disclosed in the prior art as being useful for the conversion of different organic feed stock to maleic anhydride.

In general, it is therefore known to prepare the active catalyst species through a multi-step procedure which comprises:

(a) synthesis of a vanadyl hydrogen phosphate as precursor by contacting V-containing compounds, phosphorus containing compounds and optionally promoter component containing compounds under conditions sufficient to reduce the pentavalent vanadium to the tetravalent vanadium, (b) transformation of the vanadyl hydrogen phosphate precursor into the active catalyst substantially containing vanadyl pyrophosphate by calcination and, finally, (c) aging the active catalyst under reaction conditions.

One of the most critical steps in the catalyst preparation is the calcination procedure, i.e., the transformation of the vanadyl hydrogen phosphate precursor into the active catalyst substantially containing vanadyl pyrophosphate.

U.S. Pat. No. 5,137,860 discloses a process for the transformation of a vanadium/phosphorus mixed oxide oxidation catalyst precursor into the active catalyst for the partial oxidation of non-aromatic hydrocarbons to maleic anhydride. The calcination of the precursor material is performed by a three-stage heat treatment comprising (a) an initial heat up stage and an atmosphere selected from air, steam, inert gas and mixtures thereof, (b) a rapid heat up stage at a programmed heat-up rate in a molecular oxygen/steam containing atmosphere and (c) a maintenance finishing stage, first in a molecular oxygen/steam containing atmosphere and thereafter in a non-oxidizing steam containing atmosphere.

According to this disclosure the calcination takes place in a fixed bed at atmospheric pressure conditions. As the splitting off of water during the calcination is endothermic, it was found that remarkable temperature gradients in the fixed bed occur. This inhomogenity in the temperature profile finally lead to a lower performance and decreased attrition resistance of the catalytic system.

BROAD DESCRIPTION OF THE INVENTION

An object of the invention therefore is to avoid the disadvantages of the state of the art catalytic system and to provide an improved process for the transformation of a vanadium/phosphorus mixed oxide catalyst precursor into the active catalyst for the production of maleic anhydride.

Another object of the invention is to provide a catalyst with optimal performance in the conversion of a non-aromatic hydrocarbon to maleic anhydride. Still another object of the invention is to provide an improved process for the preparation of maleic anhydride. Other objects and advantages of the invention are achieved by the processes of the invention.

The objectives and advantages of the invention are achieved with the new process of the invention for the transformation of a vanadium/phosphorus mixed oxide catalyst precursor into the active catalyst, with the catalyst obtainable by such inventive transformation process, and with the process for the preparation of maleic anhydride applying the catalyst transformed according to the instant invention.

The inventive process comprises the transformation of a catalyst precursor represented by the formula:

$$(VO)HPO_4 \text{a } H_2O \text{ Me}_m P_p O_y \qquad \text{I}$$

wherein Me is at least one promoter element selected from the group consisting of elements from Group IA, IB, IIA, IIB, IIIA, IIIB, IVA, IVB, VA, VB, VIA, VIB AND VIIIA of the Periodic table of elements or mixtures thereof, a is a number of from about 0.3 to about 0.7, m is a number of from about 0 to about 0.3, p is a number of from about 0 to about 0.3 and y corresponds to the amount of oxygen necessary to satisfy the valence requirements of all elements present, into an active catalyst represented by the formula:

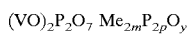

$$(VO)_2 P_2 O_7 \text{ Me}_{2m} P_{2p} O_y \qquad \text{II}$$

wherein m, p and y are as defined above, which process comprises conducting in a fluidized bed the steps:

(a) initially heating of the precursor to a temperature not exceeding about 250° C., (b) further heating under super atmospheric pressure from about 200° C. to a temperature of from at least 380° C. to 600° C., (c) maintaining the temperature reached at stage (b) under super atmospheric pressure, and (d) cooling the activated catalyst.

DETAILED DESCRIPTION OF THE INVENTION

The term "Periodic table of elements", as employed herein, refers to the Periodic table of elements published in *Römpp Chemie Lexikon* 9th edition, Georg Thieme Verlag, Stuttgart, volume 4, page 3285.

Me has the preferable meaning of lithium, zirconium, titanium, iron or niobium or of mixtures of at least two of these elements, a preferably is a number of about 0.5, m preferably is a number of from about 0 to about 0.1, and p preferably is a number of from about 0.1 to 0.2.

The phosphorus to vanadium- or P/V-atomic ratio therefore is expediently in the range of from about 1 to 1.3, preferably of from about 1.1 to about 1.2.

Catalyst precursor materials suitable for the use in the process of the instant invention are those known in the art, e.g., from U.S. Pat. No. 4,594,433, U.S. Pat. No. 5,137,860 or U.S. Pat. No. 4,668,652.

The preparation of the precursors, accordingly, includes reaction of the vanadium component, the phosphorus component and optionally the promoter component in either aqueous or organic medium. Organic reaction media, such as, a primary and a secondary alcohol or mixtures thereof are usually preferred. Most preferred is isobutyl alcohol or benzyl alcohol or mixtures thereof. Depending on the preparation conditions, the alcohol may remain trapped or intercalated to a remarkable content in the precursor structure.

Although well known in the art, the vanadium component of the precursor can be obtained from a trivalent, a tetravalent or a pentavalent vanadium compound. Representative examples, although not limiting, are vanadium trichloride, vanadium tetrachloride, vanadium dioxide, vanadium pentoxide or vanadium oxytribromide. Vanadium pentoxide is the preferred compound.

Examples of the phosphorus compound, although not limiting, are phosphorus acid or phosphoric acid.

Depending on the valence of the vanadium compound, the reaction can either be conducted under non-oxidizing conditions or under reducing conditions in order to reduce a pentavalent vanadium compound to the tetravalent form.

The catalyst precursor once prepared, recovered and dried, is in view of its activation treatment in the fluidized bed according to the invention, preferably formed into defined structures with defined properties as to attrition resistance or mechanical properties. Such procedures in general include a wet grinding process of the dried precursor to a particle size of less than 10 $\mu$m, preferably less than 3 $\mu$m. Additives may be added at this stage to improve resistance to attrition following the disclosure of, e.g., U.S. Pat. No. 4,511,670. Following this previous art, a recovery step, e.g., by spray drying, calcinating, additional grinding in the presence of a controlled amount of an acid, typically phosphoric acid, and finally recovering and forming of the precursor material by, e.g., spray drying may follow. Preferably the precursor is collected in a spherical shape, which form is most suitable for its use in a fluidized bed reactor.

The transformation of the precursor material as defined by general formula I into the active catalyst in general comprises four steps, which are conducting in a fluidized bed, the steps:

(a) initially heating the precursor to a temperature not exceeding about 250° C., (b) further heating under super atmospheric pressure from about 200° C. to a temperature of from at least 380° C. to 600° C., (c) maintaining the temperature reached at stage (b) under super atmospheric pressure, and (d) cooling the activated catalyst.

According to the invention, the transformation into the active catalyst takes place in a fluidized bed which expediently means under conditions which allow optimal fluidization of the catalyst bed. Such conditions are preferably expressed with the superficial velocity which is defined as the volume of gaseous feed at the current temperature and pressure conditions per second expressed in $m^3s^{-1}$ divided by the surface area of the catalyst bed expressed in $m^2$ leading to the superficial velocity expressed in $ms^{-1}$.

The superficial velocity is usually adjusted to a range of from about 0.01 $ms^{-1}$ to 0.5 $ms^{-1}$, preferably from about 0.02 $ms^{-1}$ to 0.2 $ms^{-1}$, as a rule during the whole phase of transformation of the precursor into the active catalyst.

Within the initial heat-up stage (a), the precursor is heated in a conventional atmosphere, e.g., like air, steam, inert gas or mixtures thereof, under atmospheric pressure or super atmospheric pressure and at any convenient heat up rate to a temperature not to exceed about 250° C.

Super atmospheric pressure in the following is expressed as absolute pressure.

In a preferred embodiment, the precursor is heated in air under super atmospheric pressure of at least 1.1 bar, more preferably 2 bar to 3 bar, at a heat up rate of about 1° C./minute to 5° C./minute to a temperature not to exceed about 200° C.

Within the activation stages (b) and (c), super atmospheric pressure is a mandatory parameter which surprisingly has the effect of further improving the performance of the catalytic system. Expediently, in these stages, super atmospheric pressure of at least 1.1 bar, preferably of from about 2 to about 3 bar is applied.

Stage (b) comprises a further heat up stage where the temperature reached in stage (b) is further increased from about 200° C. to a temperature of at least 380° C. to not to exceed about 600° C., preferably increased from about 200° C. to about 400° C. to 450° C., at a controlled heat up rate, in a defined atmosphere and under the fluidized bed and pressure conditions as described herein before.

Expediently a heat up rate of from about 0.1° C./minute to about 10° C./minute, preferably of from about 1° C./minute to about 4° C./minute, is selected.

The atmosphere necessary for stage (b) is a composition of oxygen or an oxygen containing gas, of an inert gas and of steam, expediently containing 1 to 20 percent by volume, preferably 2 to 10 percent by volume, of oxygen, 10 to 80 percent by volume, preferably 30 to 70 percent by volume, of steam (calculated as $H_2O$) and the balance inert gas. The source of oxygen can either be air or molecular oxygen, preferably air. As the inert gas, nitrogen or a noble gas like helium or argon can be applied.

Within the isothermal stage (c) the temperature reached in stage (b) is maintained over at least 0.5 hours, preferably for a period of 1 to 5 hours, in a controlled atmosphere and under the fluidized bed and pressure conditions as described herein before.

The atmosphere necessary for stage (c) is a composition of steam and of an inert gas and, if necessary, of oxygen or an oxygen containing gas, expediently containing 10 to 80 percent by volume, preferably 30 to 70 percent by volume of steam (calculated as $H_2O$) and 0 to 20 percent by volume, preferably 2 to 10 percent by volume, of oxygen and the balance inert gas.

The source of oxygen can either be air or molecular oxygen, preferably air. As the inert gas, nitrogen or a noble gas like helium or argon can be applied.

Within the cooling stage (d), the now activated catalyst is brought to ambient temperature. Although the conditions are not critical, it is preferred to perform this stage in an inert atmosphere and under the fluidized bed and pressure conditions as described herein before. The cooling rate preferably should not exceed 5° C./minute.

After this transformation performed according to the invention, the catalyst is ready to be applied for the conversion of non-aromatic hydrocarbons to maleic anhydride. Surprisingly, and this is a further important aspect of the invention, the catalyst needs no further aging under process conditions. The catalyst exhibits immediate activity and selectivity right from the beginning of the conversion providing excellent yields of maleic anhydride. The process for this conversion of non-aromatic hydrocarbons to maleic anhydride is well known in the art, e.g., from U.S. Pat. No. 4,594,433, U.S. Pat. No. 5,137,860 or U.S. Pat. No. 4,668,652.

In general, the non-aromatic hydrocarbon is converted with oxygen or an oxygen containing gas at a temperature from about 320° C. to 500° C. to maleic anhydride. The non-aromatic hydrocarbon is expediently selected from a saturated or unsaturated $C_4$ to $C_{10}$ hydrocarbon or mixtures thereof. The most preferred hydrocarbon is n-butane. The feed gas is as a rule composed of a mixture of the hydrocarbon and of the oxygen or oxygen containing gas, preferably air having a ratio oxygen to hydrocarbon as a rule of from 15:1 to 1:1.

The conversion can take place in a fixed bed or fluidized bed reactor, but in particular is performed in a fluidized bed reactor.

The following examples are given by way of illustration only and are not construed as limiting since various modifications within the spirit of the invention are apparent to those skilled in the art from this description.

EXAMPLE 1 (Comparison)

Into a three-necked flask, capacity 5 liters, fitted with a thermometer, a mechanical stirrer, a glass distillation packed column with reflux condenser and a Dean-Stark water separator, are introduced 2 liters of isobutanol and 404 g of $H_3PO_4$ (100 percent). The mixture is brought to reflux and then a suspension of 326 g of $V_2O_5$ in 1000 ml of isobutanol is slowly added (in about 1 hour). During addition of the $V_2O_5$, a quantity of isobutanol equal to that added with $V_2O_5$ is distilled, thus removing from the reaction mixture the water that forms during the reaction. At the end of the addition of $V_2O_5$, the reflux is continued for another two hours, thus separating further reaction water. The slurry is cooled and the blue solid is filtered and dried at 140° C. In this manner, the V-P-O complex oxide precursor of the catalyst is obtained. The catalyst precursor once prepared is formed into a structure with defined properties of attrition resistance by spray drying as described in U.S. Pat. No. 4,654,425 (Example 1). The material recovered from spray drying was loaded in stainless steel baskets, and put in a forced ventilation oven. An atmosphere of $N_2$ was maintained in the oven during the calcination and the precursor was heated at a programmed heating rate of about 9° C./minute from room temperature to 550° C. At 550° C., the catalyst was kept under isothermal conditions for 5 hours, followed by cooling down to room temperature. This procedure is referred to as the standard procedure of calcination.

EXAMPLE 2 (Comparison)

This example illustrates the transformation of a vanadium phosphorus oxide precursor prepared according to Example 1 into an active catalyst in accordance with the procedure described in Example 3, Part D, of U.S. Pat. No. 5,137,860. The material recovered from spray drying was loaded into a stainless steel tray and placed in a box oven. The precursor was heated with the hydrothermal treatment according to the following procedure:

(a) from 25° C. to 275° C. in air with no control of the heat-up stage;

(b) from 180° C. to 425° C. in a mixture of air (75 mol percent) and steam (25 mol percent) at a programmed rate of 4° C./minute;

(c) isothermal step at 425° C. with the same mixture as above for 1 hour;

(d) isothermal step at 425° C. in nitrogen (50 mol percent) and steam (50 mol percent), for 6 hours.

EXAMPLE 3 (Comparison)

The procedure hereinafter described is referred to as the hydrothermal method of calcination in a fluid bed at atmospheric pressure. The procedure consists of a thermal treatment in the presence of steam. The treatment was carried out at temperatures not higher than 450° C. The material recovered from spray drying was loaded into a stainless steel fluid bed reactor and treated at atmospheric pressure with the hydrothermal treatment according to the following procedure:

(a) from 25° C. to 180° C. in air in 40' (minutes);

(b) from 180° C. to 425° C. in a mixture of air (27 volume percent) and steam (73 volume percent) at a programmed rate of 1.5° C./minute;

(c) isothermal step at 425° C. with the same mixture as above for 2 hours;

(d) isothermal step at 425° C. in nitrogen (27 volume percent) and steam (73 volume percent), for 3 hours;

(e) cooling in a mixture of nitrogen and steam.

EXAMPLE 4 (Invention)

The procedure hereinafter described is referred to as the hydrothermal method of calcination in a fluid bed under pressure. The procedure consists of a thermal treatment in the presence of steam. The treatment was carried out at temperatures not higher than 450° C. The material recovered from spray drying was loaded into a stainless steel fluid bed reactor and treated with the hydrothermal treatment under pressure (3 bar) and maintaining a superficial velocity of 0.03 $ms^{-1}$ according to the following procedure:

(a) from 25° C. to 180° C. is air, at a programmed rate of 4° C./minute;

(b) from 180° C. to 425° C. in a mixture of air (70 percent volume) and steam (30 percent volume) at a programmed rate of 1.5° C./minute;

(c) isothermal step at 425° C. with the same mixture as above for 2 hours;

(d) isothermal step at 425° C. in nitrogen (70 percent volume) and steam (30 percent volume) for 3 hours;

(e) cooling in a mixture of nitrogen and steam at a programmed rate of 2° C./minute.

EXAMPLE 5 (Invention)

The precursor was treated as in Example 4, except that the superficial velocity was 0.05 $ms^{-1}$.

EXAMPLE 6 (Invention)

The precursor was treated as in Example 4, except for the step (d) which was carried out in a mixture of nitrogen and steam for 6 hours.

EXAMPLE 7 (Invention)

The precursor was treated as in Example 4, except that an amount of oxygen in feed was 4 percent volume. The activity test was performed as in Example 1 and the catalytic behavior is given in Table 1.

Testing of the activated catalysts in the conversion of n-butane to maleic anhydride:

The catalytic tests were done in a fluid bed pilot-plant, glass, plug-flow reactor at atmospheric pressure, which was loaded with 500 ml of catalyst. The products were collected and absorbed in water and analyzed by means of gas chromatography. The performance of the catalysts was determined on the basis of the weight of butane fed to the reactor, amount of maleic anhydride (MA) recovered in the wash-water (acidimetry) and the amount of butane in the off gases during a specified period of time.

In order to provide a basis for comparison, the following conditions were maintained during the activity tests:

Reaction temperature: 360° to 440° C.
n-Butane conc. in feed: 4 volume percent.
Air flow rate: 75 Nl/h.
Superficial velocity: 0.03 ms$^{-1}$.

The reaction conditions and the results are recorded in the following Table which reports the temperature at which 81 percent n-butane conversion is achieved, and the yield and selectivity to maleic anhydride at this conversion.

TABLE I

| catalyst according to Example: | Temperature °C. | MA yield % | MA selectivity % |
|---|---|---|---|
| 1 (comparison) | 425° C. | 52.3 | 64.6 |
| 2 (comparison) | 430° C. | 53.4 | 65.9 |
| 3 (comparison) | 415° C. | 55.1 | 68.0 |
| 4 | 420° C. | 57.5 | 71.0 |
| 5 | 425° C. | 57.9 | 70.5 |
| 6 | 420° C. | 56.9 | 70.2 |
| 7 | 425° C. | 58.1 | 71.7 |

What is claimed is:

1. A process for the transformation of a catalyst precursor represented by the formula:

$$(VO)HPO_4 a\ H_2O\ Me_m P_p O_y \qquad I$$

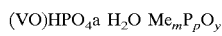

wherein Me is at least one promoter element selected from the group consisting of elements from Group IA, IB, IIA, IIB, IIIA, IIIB, IVA, IVB, VA, VB, VIA, VIB AND VIIIA of the Periodic table of elements or mixtures thereof, a is a number of from about 0.3 to about 0.7, m is a number of from about 0 to about 0.3, p is a number of from about 0 to about 0.3, and y corresponds to the amount of oxygen necessary to satisfy the valence requirements of all elements present, into an active catalyst represented by the formula:

$$(VO)_2 P_2 O_7\ Me_{2m} P_{2p} O_y \qquad II$$

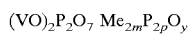

wherein m, p and y are as defined above, the process comprising, conducting in a fluidized bed, the steps:

(a) initially heating the precursor to a temperature not exceeding about 250° C., (b) further heating under super atmospheric pressure from about 200° C. to a temperature of from at least 380° to 600° C., (c) maintaining the temperature reached at stage (b) under super atmospheric pressure, and (d) cooling the activated catalyst.

2. The process according to claim 1 wherein super atmospheric pressure is maintained over all of steps (a), (b), (c) and (d).

3. The process according to claim 2 wherein super atmospheric pressure of at least 1.1 bar is applied.

4. The process according to claim 3 wherein super atmospheric pressure of from about 2 bar to about 3 bar is applied.

5. The process according to claim 4 wherein the fluidized bed is run with a superficial velocity adjusted in the range of from about 0.01 ms$^{-1}$ to 0.5 ms$^{-1}$.

6. The process according to claim 5 wherein step (a) comprises initially heating the precursor to a temperature not exceeding 200° C.

7. The process according to claim 6 wherein step (a) comprises initially heating the precursor in an atmosphere of air.

8. The process according to claim 7 wherein step (b) comprises further heating from about 200° C. to about 400° to 450° C. by applying a heat up rate of from about 0.1° C./minute to 10° C./minute.

9. The process according to claim 7 wherein step (b) comprises further heating in an atmosphere composed of 1 to 20 percent by volume of oxygen or of an oxygen-containing gas, of 10 to 80 percent by volume of steam and of the balance being inert gas.

10. The process according to claim 9 wherein step (c) comprises maintaining the temperature reached in step (b) in an atmosphere composed of 0 to 20 percent by volume of oxygen or of an oxygen containing gas, of 10 to 80 percent by volume of steam and of the balance being inert gas.

11. The process according to claim 1 0 wherein step (d) comprises cooling the activated catalyst in an inert atmosphere at a rate not to exceed 5° C./minute.

12. The process according to claim 1 wherein super atmospheric pressure of at least 1.1 bar is applied.

13. The process according to claim 1 wherein super atmospheric pressure of from about 2 bar to about 3 bar is applied.

14. The process according to claim 1 wherein the fluidized bed is run with a superficial velocity adjusted in the range of from about 0.01 ms$^{-1}$ to 0.5 ms$^{-1}$.

15. The process according to claim 1 wherein step (a) comprises initially heating the precursor to a temperature not to exceed 200° C.

16. The process according to claim 15 wherein step (a) comprises initially heating the precursor in an atmosphere of air.

17. The process according to claim 1 wherein step (b) comprises further heating from about 200° C. to about 400° to 450° C. by applying a heat up rate of from about 0.1° C./minute to 10° C./minute.

18. The process according to claim 16 wherein step (b) comprises further heating in an atmosphere composed of 1 to 20 percent by volume of oxygen or of an oxygen-containing gas, of 10 to 80 percent by volume of steam and of the balance being inert gas.

19. The process according to claim 1 wherein step (c) comprises maintaining the temperature reached in step (b) in an atmosphere composed of 0 to 20 percent by volume of oxygen or of an oxygen containing gas, of 10 to 80 percent by volume of steam and of the balance being inert gas.

20. The process according to claim I wherein step (d) comprises cooling the activated catalyst in an inert atmosphere at a rate not to exceed 5° C./minute.

21. An active catalyst represented by the formula:

$$(VO)_2 P_2 O_7 Me_{2m} P_{2p} O_y \qquad II$$

wherein m is a number of from about 0 to 0.3, p is a number of from about 0 to 0.3, and y corresponds to the amount of oxygen necessary to satisfy the valence requirements of all elements present, said active catalyst having been prepared by process comprising, conducting in a fluidized bed, the steps:

(a) initially heating a catalyst precursor to a temperature not exceeding about 250°, the catalyst precursor being represented by the formula:

$$(VO)HPO_4 a\ H_2O\ Me_m P_p O_y \qquad I$$

wherein Me is at least one promoter element selected from the group consisting of elements from Group IA, IB, IIA, IIB, IIIA, IIIB, IVA, IVB, VA, VB, VIA, VIB and VIIIA of the Periodic table of elements or mixtures thereof, a is a number of from about 0.3 to about 0.7, and m, p and y are defined above, (b) further heating under super atmospheric pressure from about 200° C. to a temperature of from at least 380° to 600° C., (c) maintaining the temperature reached at stage (b) under super atmospheric pressure, and (d) cooling the activated catalyst.

22. A process for the production of maleic anhydride which comprises converting a feeding gas composed of non-aromatic hydrocarbon and of oxygen or of an oxygen containing gas in the presence of an active catalyst at a temperature of from about 320° to about 500° C., the active catalyst represented by the formula:

$$(VO)_2P_2O_7\ Me_{2m}P_{2p}O_y \qquad II$$

wherein m is a number from about 0 to 0.3, p is a number from about 0 to 0.3, and y corresponds to the amount of oxygen necessary to satisfy the valence requirements of all elements present, said active catalyst having been prepared by process comprising, conducting in a fluidized bed, the steps:

(a) initially heating a catalyst precursor to a temperature not exceeding about 250° C., the catalyst precursor represented by the formula:

$$(VO)HPO_4 a\ H_2O\ Me_mP_pO_y \qquad I$$

wherein Me is at least one promoter element selected from the group consisting of elements from Group IA, IB, IIA, IIB, IIIA, IIIB, IVA, IVB, VA, VB, VIA, VIB and VIIIA of the Periodic table of elements or mixtures thereof, a is a number of from about 0.3 to about 0.7, and m, p and y are defined above, (b) further heating under super atmospheric pressure from about 200° C. to a temperature of from at least 380° to 600°, (c) maintaining the temperature reached at stage (b) under super atmospheric pressure, and (d) cooling the activated catalyst.

23. An active catalyst represented by the formula:

$$(VO)_2P_2O_7\ Me_{2m}P_{2p}O_y \qquad II$$

wherein m is a number of from about 0 to about 0.3, p is a number of from about 0 to about 0.3, and y corresponds to the amount of oxygen necessary to satisfy the valence requirements of all elements present, said active catalyst having been prepared by a process comprising, conducting in a fluidized bed which is run with a superficial velocity adjusted in the range of from about 0.01 ms$^{-1}$ to 0.5 ms$^{-1}$, the steps:

(a) initially heating a catalyst precursor to a temperature not exceeding 200° C. in an atmosphere of air, the catalyst precursor represented by the formula:

$$(VO)HPO_4 a\ H_2O\ Me_mP_pO_y \qquad I$$

wherein Me is at least one promoter element selected from the group consisting of elements from Group IA, IB, IIA, IIB, IIIA, IIIB, IVA, IVB, VA, VB, VIA, VIB and VIIIA of the Periodic table of elements or mixtures thereof, a is a number of from about 0.3 to 0.7, and m, p, and y are defined above, (b) further heating from about 200° C. to about 400° to 450° C. by applying a heat up rate of from about 0.1° C./minute to 10° C./minute in an atmosphere composed of 1 to 20 percent by volume of oxygen or of an oxygen-containing gas, of 10 to 80 percent by volume of steam and of the balance being inert gas, (c) maintaining the temperature reached in step (b) in an atmosphere composed of 0 to 20 percent by volume of oxygen or of an oxygen containing gas, of 10 to 80 percent by volume of steam and of the balance being inert gas, and (d) cooling the activated catalyst in an inert atmosphere at a rate not to exceed 5° C./minute, super atmospheric pressure of from about 2 bar to about 3 bar is applied and maintained in all of steps (a), (b), (c) and (d).

24. A process for the production of maleic anhydride which comprises converting a feeding gas composed of a non-aromatic hydrocarbon and of oxygen or of an oxygen containing gas in the presence of an active catalyst at a temperature of from about 320° to about 500° C., the active catalyst represented by the formula:

$$(VO)_2P_2O_7\ Me_{2m}P_{2p}O_y \qquad II$$

wherein m is a number from about 0 to about 0.3, p is a number of from about 0 to about 0.3, and y corresponds to the amount of oxygen necessary to satisfy the valence requirements of all elements present, said active catalyst having been prepared by process comprising, conducting in a fluidized bed which is run with a superficial velocity adjusted in the range of from about 0.01 ms$^{-1}$ to 0.5 ms$^{-1}$, the steps:

(a) initially heating a catalyst precursor to a temperature not exceeding 200° C. in an atmosphere of air, the catalyst precursor represented by the formula:

$$(VO)HPO_4 a\ H_2O\ Me_mP_pO_y \qquad I$$

wherein Me is at least one promoter element selected from the group consisting of elements from Group IA, IB, IIA, IIB, IIIA, IIIB, IVA, IVB, VA, VB, VIA, VIB and VIIIA of the Periodic table of elements or mixtures thereof, a is a number of from about 0.3 to about 0.7, and m, p and y are defined above, (b) further heating from about 200° C. to about 400° to 450° C. by applying a heat up rate of from about 0.1° C./minute to 10° C./minute in a atmosphere composed of 1 to 20 percent by volume of oxygen-containing gas, of 10 to 80 percent by volume of steam and of the balance being inert gas, (c) maintaining the temperature reached in step (b) in an atmosphere composed of 0 to 20 percent by volume of oxygen or of an oxygen containing gas, of 10 to 80 percent by volume of steam and of the balance being inert gas, and (d) cooling the activated catalyst in an inert atmosphere at a rate not to exceed 5° C./minute, super atmospheric pressure of from about 2 bar to about 3 bar is applied and maintained in all of steps (a), (b), (c) and (d).

* * * * *